United States Patent [19]
Wang

[11] Patent Number: 5,866,150
[45] Date of Patent: Feb. 2, 1999

[54] ANTIBACTERIALLY ACTIVE EXTRACTS FROM THE MARINE ALGAE CHAETOCEROS AND METHODS OF USE

[75] Inventor: Jaw-Kai Wang, Honolulu, Hi.

[73] Assignee: Aquaculture Technology Incorporated, Honolulu, Hi.

[21] Appl. No.: 618,861

[22] Filed: Mar. 20, 1996

[51] Int. Cl.$^6$ ................................................. A01N 25/00
[52] U.S. Cl. ........................ 424/405; 424/93.1; 424/93.7; 435/946; 514/560
[58] Field of Search ................................. 424/405, 93.1, 424/93.7, 195.1; 435/946; 800/DIG. 7; 514/560

[56] References Cited

U.S. PATENT DOCUMENTS

| | | | |
|---|---|---|---|
| 1,901,434 | 3/1933 | Cade et al. | 514/560 |
| 3,601,094 | 8/1971 | Kittaka . | |
| 3,916,832 | 11/1975 | Sweeney . | |
| 3,939,279 | 2/1976 | Kawano et al. . | |
| 4,755,610 | 7/1988 | Moore et al. . | |
| 4,870,185 | 9/1989 | Bonjouklian et al. . | |
| 4,946,835 | 8/1990 | Hirsch et al. . | |
| 4,968,799 | 11/1990 | Hutt, Jr. et al. . | |
| 4,977,154 | 12/1990 | Sanchez et al. . | |
| 5,063,160 | 11/1991 | Holmes . | |
| 5,144,907 | 9/1992 | Dabinett . | |
| 5,155,032 | 10/1992 | Tanaka et al. . | |
| 5,168,060 | 12/1992 | Holmes . | |
| 5,227,300 | 7/1993 | Holmes et al. . | |
| 5,292,650 | 3/1994 | Bonjouklian et al. . | |
| 5,340,594 | 8/1994 | Barclay | 426/49 |
| 5,358,713 | 10/1994 | Shimamura . | |
| 5,366,890 | 11/1994 | Bonjouklian et al. . | |
| 5,401,647 | 3/1995 | Tanaka et al. . | |
| 5,604,258 | 2/1997 | Fewante et al. | 514/560 |
| 5,656,667 | 8/1997 | Brevuk et al. | 514/560 |

FOREIGN PATENT DOCUMENTS

| | | |
|---|---|---|
| 0132089 | 1/1985 | European Pat. Off. . |
| 0099432 | 6/1983 | Japan . |
| 58-99432 | 6/1983 | Japan . |
| 02129113 | 5/1990 | Japan . |

OTHER PUBLICATIONS

Marie–odile et al. Phyto chemistry 36(31)691–3 1994 Fatty Acid Composition of some Marine Microalgae.

Franke et al: Int. Road Ingredients (4) 41–5 1994 polyunsaturated fatty acids from microalgae.

Ohta et al.: J. Appl. Phycol. 7(2), 121–7 1995 Antibiotic effect.

*Primary Examiner*—Neil S. Levy
*Attorney, Agent, or Firm*—Hoffmann & Baron, LLP

[57] ABSTRACT

The present invention relates to the use of extracts obtained from the marine algae Chaetoceros as antibacterially active agents and to compositions containing such agents for use against pathogenic bacteria. This invention also relates to a method of depurating an aquiculture using as a feed source the marine algae Chaetoceros.

8 Claims, No Drawings

5,866,150

ANTIBACTERIALLY ACTIVE EXTRACTS FROM THE MARINE ALGAE CHAETOCEROS AND METHODS OF USE

FIELD OF THE INVENTION

The present invention relates to the use of extracts obtained from the marine algae Chaetoceros as antibacterially active agents and to compositions containing such agents for use against pathogenic bacteria. This invention also relates to a method of depurating crustaceans, bivalves and mollusks by using the marine algae Chaetoceros spp. as part of the feed. This invention also relates to a method of maintaining a pathogenic vibrio free environment for the cultivation of marine aquatic animals, particularly shrimp, by maintaining sufficient Chaetoceros spp. density in the cultivating water system.

BACKGROUND OF THE INVENTION

The contamination of seabeds has become more problematic as the environment has gradually become more polluted. Pathogenic microorganisms are well known to infect seabeds, which are exposed to toxic waste and other undesirable pollutants. Controlled cultivation of fish, mollusks, crustaceans and other aquianimals has become more prevalent in view of the ever growing scarcity of uncontaminated sources. Such contamination concerns are further complicated by the fact that a number of bacteria have become multi-drug resistant as a result of improper and/or overuse of antibiotics. The emergence of antibiotic-resistant bacteria has become more widespread and has resulted in the necessity to track the spread of such resistant strains and to the initiation of research efforts which seek alternative antibacterial agents which can be used to combat such resistant strains.

Pathogenic *Vibrio vulnificus* is commonly found in raw oysters and has been associated with the occurrence of shrimp diseases, either as a direct cause of disease, or as a carrier of virus or both. Additionally, bacteria such as *Staphylococcus aureus* has become resistant to methicillin, leaving only vancomycin as the remaining effective antibiotic against this strain. Virulent strains of enterococcus have emerged which are vancomycin resistant causing an alarming realization of the need to find new antibiotics against this organism. Such pathogenic bacteria are known to be extremely dangerous to humans.

The present invention provides a solution to deputation of bivalves and mollusks by using the marine algae Chaetoceros as a food source for the aquianimals. Chaetoceros spp. provide natural antibiotic properties which cleanse the aqui-animal from pathogenic vibrio, thereby making the harvested seafood safe for consumption.

Additionally, there is a need for new antibiotics and pharmaceutical compositions based thereon which are effective against a broad spectrum of bacteria and which are particularly useful against known multi-drug resistant strains of bacteria, including methicillin resistant *Staphylococcus aureus*, vancomycin resistant enterococcus, *Vibrio cholerae* and *Vibrio vulnificus*. Additionally, there is a need for the development of new antibacterially effective agents which can be made inexpensively and which are safe for use in mammals, aquianimals and the like. The present invention provides antibacterial agents which are based on the extracts of the marine algae Chaetoceros. Fractions and isolates of Chaetoceros spp. extracts have been shown to provide antibacterial activity and, in particular are active against methicillin resistant *Staphylococcus aureus*, vancomycin resistant enterococcus bacteria, *vibrio chlorae* and *vibrio vulnificus*. The antibacterially effective extracts of the Chaetoceros algae are believed to either occur naturally in the unicellular algae or are produced by the algae in response to the presence of bacterium and other algae that compete against Chaetoceros for living space.

Pharmaceutical compositions and methods of treating mammals by administering bacterially effective amounts of one or more of the isolates of the Chaetoceros spp. extract are claimed herein.

SUMMARY OF THE INVENTION

The present invention relates to the use of extracts from the marine algae Chaetoceros as antibacterial agents and novel pharmaceutical compositions based thereon using one or more of the antibacterially effective isolates from these extracts. Additionally, a method of treating mammals having bacterial infection by administering an antibacterially effective amount of one or more isolates or compounds extracted from the extract of Chaetoceros is also contemplated.

Additionally, a method of depurating cultured aquatic animals such as oysters, clams, mussels, scallops, shrimp and the like is also contemplated.

Thus, in one embodiment a composition including an antibacterially active extract obtained from the marine algae Chaetoceros is contemplated. The extracts obtained from this algae have been found to be active against a number of virulent bacteria including methicillin resistant *Staphylococcus aureus*, vancomycin resistant enterococcus, *Vibrio vulnificus, vibrio choleral* and *Listeria monocytogene*. The extract itself, which includes a number of compounds, has been shown to have activity against bacteria, including those mentioned above. Additionally, a number of isolates have been extracted or fractionated from the crude extract. These isolates have also demonstrated antibacterial activity against bacteria and these particularly virulent strains mentioned above. Two compounds have been specifically identified which have antibacterial activity. The compounds labeled II and III are fatty acids which have heretofore not been known to have antibacterial activity against the above bacteria.

The present invention also contemplates pharmaceutical compositions which are made to include the extract or one or more of its isolates obtained from the marine algae Chaetoceros, together with a pharmaceutically accepted carrier. The isolates may be used singly or one or more of the pure compounds may be combined as a mixture. Pharmaceutical acceptable derivatives and salts of these compounds and isolates are contemplated. A method of treating bacterial infections by administering the pharmaceutical composition containing one or more antibacterially active isolates is also contemplated.

In addition to the novel compounds and pharmaceutical compositions described herein, the present invention also contemplates a method of depurating bivalves and mollusks which are contaminated with bacteria. The method includes introducing the marine algae Chaetoceros as a feed for an aquianimal in a sufficient amount and for sufficient time to effectuate depuration. Due to the natural antibacterial activity of the marine algae Chaetoceros, the exposure and/or ingestion of the algae as feed by the aquianimal produces a depurating effect and cleanses the aquianimal of bacteria such that the aquianimal can be further cultured and grown in a healthy environment, and finally be consumed as a food source. Thus, co-culturing of the Chaetoceros algae along with the aquianimal is included in the present invention in order to bring about the desired effect of both feeding the aquianimal and depurating the aquiculture of bacteria.

The eluant used to obtain the fractions and measure its activity against the specified bacteria is tabulated in Tables II, III and IV herein. Various fractions obtained from gradient elution have been shown to have activity.

DETAILED DESCRIPTION OF THE INVENTION

Depurating aquianimals such as oysters, mussels, clams, snails, scallops, shrimp and the like have generally not been effective with regard to the elimination of pathogenic vibrio. The use of antibiotics in the depuration of an aquianimal has not received approval from the FDA. The present invention provides both a food source and simultaneous cleansing of an aquianimal due to the natural antibiotic properties exhibited by the algae Chaetoceros in the presence of bacteria. During experimentation in a controlled-environment with oyster cultures which were contaminated with bacteria, it was discovered that the introduction of the Chaetoceros algae as a food source, when used in a sufficient amount and for a sufficient time, caused depuration of the oysters and decontamination of pathogenic bacteria, including *Vibrio vulnificus* and *Vibrio cholerae* present therein. In the course of analyzing this effect, the Chaetoceros algae was studied more closely for its contribution to the natural antibacterial cleansing of the oysters in the culture medium.

The Chaetoceros algae is a single celled organism, the main body of which is shaped liked a petri dish. When viewed from the side, individual cells appear square, having dimensions of about 12 to about 14 microns long and about 15 to about 17 microns wide, with spines protruding from the corners. The cells may form chains of about 10 to 20 cells which may reach up to 200 microns in length. The chains are formed by interconnecting the spines of adjacent cells.

When cultured with strong aeration, Chaetoceros does not form colonies. Large cultures are brown in appearance and individual cells are golden brown in color, surrounded by a translucent cell wall. The algae is known to be a food source for rotifers, clams, oysters, and larval shrimps. The taxonomy of Chaetoceros is described as follows:

Division: Bacillariophyta

Class: Diatomatae

Order: Centrales

Suborder: Biddulphiincae

Family: Chaetoceraccae

Genus: Chaetoceros

The genus Chaetoceros is described usually as an oval or circular section which, in girdle view, appears quadrangular with straight sides and concave, flat or weakly convex ends. The cell has a valve consisting of more or less a flat end surface (the valve surface) and a cylindrical part (the valve mantle) which are bound together without a seam. The cell is valve-bearing at each end of the long axis (apical axis) on the corners, and has a long thick or thin bristle, sometimes called an awn. The opposite bristles of neighboring cells touch one another, usually directly but sometimes by a bridge, and become firmly fused together. By fusion of the bristles, the cells are formed into chains, usually with large or small apertures or foramina between the cells. In some species the length of the chain is limited by the formation of special end-cells, their outer bristles not being connected with neighboring cells and differing from the others, often being shorter and thicker and nearly more parallel with the chain axis. These end-cells are believed to serve certain purposes when the chain floats.

The cell wall of the Chaetoceros algae is formed of two halves and one or two girdle bands. Intercalary bands are present in some species, but are usually difficult to see without special methods. The valve or chain axis runs through the valves from center to center. The cell cytoplasm forms either only as a thin sack along the cell wall or it can fill the greater part of the inside of the cell. The nucleus may be against the cell wall or be central to the cell. Chromatophores are present, numbering from one to several and may be small or large. Resting spores are formed in most of the neritic species, usually in the cylindrical part near the girdle band of the mother cell, one to each cell. The valves of the spores are often armed with spines or spicules, sometimes only on one valve, sometimes on both, but rarely at the sides.

After observing the antibacterial depuration of oysters when Chaetoceros was used as a feed for an oyster culture, an algal culture was developed for the purpose of determining an activity profile against bacterial microorganisms and to determine the efficacy of different fractions and extracts from the algae on bacteria. The algal cells were harvested and ground to a wet algae-paste, which was then taken into water and centrifuged to obtain a supernatant liquid. The supernatant liquid was then loaded onto a chromatography column and eluted with an aqueous gradient eluant. Various fractions were identified and tested for antibacterial activity, as was the mixture as a whole. The details of such testing will be further described herein.

For purposes of this invention, the term "extract" will include compounds, isolates, fractions as well as mixtures thereof obtained from the Chaetoceros cell. The extract can be obtained using any known method of extraction or fractionation, including the use of chromatography columns and eluants, solvent extraction and the like. For purposes of this disclosure, column chromatography has been used for its ease of use and accuracy, but commercial separation techniques which may vary from laboratory techniques are contemplated herein.

Among the isolates that have been identified as having antibacterial activity are those which correspond to the general following formula:

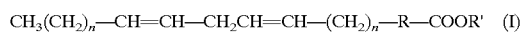

$$CH_3(CH_2)_n—CH=CH—CH_2CH=CH—(CH_2)_n—R—COOR' \quad (I)$$

wherein n is an integer from 1 to 8; when present R is $—CH=CH—(CH_2)_p$; P is an integer from 1–10; and R' is H or alkyl $C_{1-10}$; and pharmaceutically acceptable salts and derivatives thereof are also contemplated.

Among the specific compounds corresponding to this formula which have shown antibacterial properties include the following:

(Z,Z,Z)-6,9,12-Hexadecatrienoic acid (16:3Δ6,9,12) of the formula

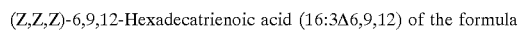
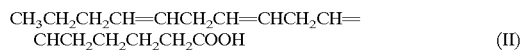

$$CH_3CH_2CH_2CH=CHCH_2CH=CHCH_2CH= CHCH_2CH_2CH_2CH_2COOH \quad (II)$$

as well as:

(Z,Z)-9,12-Hexadecadienoic acid (16:2Δ9,12) of the formula

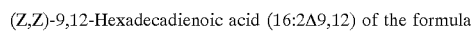
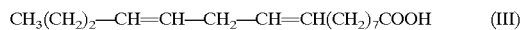

$$CH_3(CH_2)_2—CH=CH—CH_2—CH=CH(CH_2)_7COOH \quad (III)$$

The compounds of the present invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such a solubility in polar solvents, but the salts are otherwise equivalent to their respective free base forms for purposes of the invention.

Certain compounds of the invention may exist in optically active forms. All such isomers as well as mixtures thereof are intended to be included in the invention.

The compounds of the invention can be prepared and administered in a wide variety of oral and parenteral dosage forms. It will be obvious to those skilled in the art that the following dosage forms comprise as the active component either a compound of formulae I through III or a corresponding pharmaceutically acceptable salt of a compound of formulae I through III.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substance which may also act as a diluent, flavoring agent, solubilizer, lubricant, suspending agent, binder, or tablet disintegrating agent; it can also be an encapsulating material. In powders, the carrier is a finely divided solid which is an admixture with the finely divided active compound. In the tablet, the active compound is mixed with carrier having the necessary binding properties in suitable proportions and compacted in the shape and size desired. The powders and tablets preferably contain from about 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example, water or water-propylene glycol solutions for parenteral injection may be used. Such solutions are prepared so as to be acceptable to biological systems (isotonicity, pH, etc.). Liquid preparations can also be formulated in solution in an aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections, the compounds utilized in the pharmaceutical method of this invention are anticipated to be administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The Minimum Inhibition Concentration (MIC) for Compound II with respect to methicillin resistant *Staphylococcus aureus* (MRSA) is 10–15 µg/disk and 20 µg/disk for vancomycin resistant enterococcus (VRE).

It has been found that 100 µg/disk of Compound II of the present invention is active against *Pyogenes vulgaris, Carynobacter xerosis, Shigella dysenteriae, Streptococcus mitis, Streptococcus facaelis, Bacillus subtilis, Bacillus cereus*, methicliin resistant *Staphylococcus aureus* (MRSA), and vancomycin resilient enterococcus. It was also found that 100 µg/disk of Compound II is not effective against *Salmonella typhimurium* nor against *Klebsiella pneumoniae*.

It has been found that 100 µg/disk of Compound III of the present invention is active against *Bacillus sublilis*, MRSA, VRE, *Micrococcus smegmatis, Micro luteus, Streptococcus puogenes, Listeria monocytogenes, Salmonella typhimurium, Proteus vulgaris, Corynebacterium xerosis,* and *Bacillus cereus*. In addition, it has been found that Compound III is effective against *Candida albicans* at a concentration of 100 µg/disk. It was also found that 100 µg/disk of Compound III is not effective against *Shigella dysenteria* and *Klebsiella pneumoniae*.

| MINIMUM INHIBITORY CONCENTRATION OF COMPOUND III ON METHICILLIN RESISTANT *STAPHYLOCOCCUS AUREUS* (MRSA) AND VANCOMYCIN RESISTANT ENTEROCOCCUS (VRE) AFTER 24 HOURS | | |
|---|---|---|
| Concentration of Compound (µg/disk) | Inhibition Zone (mm) MRSA/VRE | Remark MRSA/VER |
| 100 | 5/3.5 | clear/fuzzy |
| 80 | 4/2.5 | clear/fuzzy |
| 60 | 3/2 | clear/fuzzy |
| 40 | 1.75/1 | clear/fuzzy |
| 20 | 1.13*/2.5 | */fuzzy |
| 15 | 1/2 | fuzzy/fuzzy |

-continued

MINIMUM INHIBITORY CONCENTRATION OF COMPOUND III
ON METHICILLIN RESISTANT *STAPHYLOCOCCUS AUREUS*
(MRSA) AND VANCOMYCIN RESISTANT ENTEROCOCCUS
(VRE) AFTER 24 HOURS

| Concentration of Compound ($\mu$g/disk) | Inhibition Zone (mm) MRSA/VRE | Remark MRSA/VER |
|---|---|---|
| 10 | <0.5/2 | fuzzy/fuzzy |
| 5 | <0.5/1 | fuzzy/fuzzy |

*The 20 $\mu$g/disk data point was used in 2 experiments yielding an average of 1.13 mm. In one experiment, the Inhibition Zone was clear; in the second experiment, it was fuzzy.

The MIC experiments indicated that concentrations of 15–20 $\mu$g/disk of compound III effectively inhibits the ability of MRSA and VRE to grow.

The following in vitro examples are given to illustrate certain embodiments of the invention, but are not intended in any way to be limiting of the effective scope or spirit of the invention as described and claimed. Observations as to activity were taken after 12 hours unless otherwise specified.

EXAMPLE I

From 201.4 liters of algae culture having a cell density ranging from $1 \times 10^6$ to $7 \times 10^6$ cells per milliliter of water, 22.5 grams of ground wet algae-paste was obtained. The wet paste was taken into 600 milliliters of water and centrifuged at 10,000 RPMs for approximately 20 minutes. The supernatant liquid was then loaded onto an Amberlite XAD-2 column (sigma, 30×7 cm) and eluted with 2.0 liters of the following gradient: (1) water, (2) 10% aqueous MeOH, and (3) 30% aqueous MeOH, (4) 50% aqueous MeOH, (5) 70% aqueous MeOH, (6) 90% aqueous MeOH, (7) MeOH and (8) $CH_2Cl_2$. These fractions were tabulated in Table II and show that identified fractions were placed in petri dish cultures of methicillin resistant *Staphylococcus aureus*. As can be seen from Table II, activity against *Staphylococcus aureus* was observed in fractions 5–7 with fraction 6 yielding the highest activity. Activity is indicated by the dark portion around the white circle of antibiotic which was introduced into the petri dish. The observations as to activity were taken after 12 hours.

Activity is indicated in fractions 5 through 8, with the highest activity being present in fraction 6. The activity of the various fractions against *Vibrio vulnificus* can be seen from the table. Activity was strongest in fractions 5 through 8, with the highest activity occurring with fraction 6.

As can be seen from Table II, the most active fractions against each of the organisms listed are fractions 5 to 8, with fraction 6 obtained from a 90% by volume aqueous methanol eluant indicating the highest activity.

All of the fractions were concentrated under reduced pressure to provide the crude material. As a result of activities observed in fractions 5 through 8, these fractions were combined and loaded onto a YMC-ODS-120A (reverse-phase silica gel, C18; 20 X 2.5 cm) eluting with the following gradient, the fraction number in the table being indicated with the same numbers: (1.1) 20% aqueous MeOH, (2.1) 40% aqueous MeOH, (3.1) 60% aqueous MeOH, (4.1) 80% aqueous MeOH, and (5.1) MeOH. Five fractions of 250 to 300 milliliters were collected and tested for activities using

TABLE II

| | | ACTIVE AGAINST | | |
|---|---|---|---|---|
| Fraction No. | Eluent | *Staphylococcus aureus*[1] | Enterococcus[2] | *Vibrio vulnificus* |
| 1 | $H_2O$ | + | -- | -- |
| 2 | 10% Aq. MeOH | -- | -- | -- |
| 3 | 30% Aq. MeOH | + | -- | -- |
| 4 | 50% Aq. MeOH | -- | -- | -- |
| 5 | 70% Aq. MeOH | + | -- | -- |
| 6 | 90% Aq. MeOH | ++ | -- | -- |
| 7 | MeOH | ++ | -- | -- |
| 8 | $CH_2Cl_2$ | + | -- | -- |
| 1 | $H_2O$ | -- | -- | -- |
| 2 | 10% Aq. MeOH | -- | -- | -- |
| 3 | 30% Aq. MeOH | -- | * | -- |
| 4 | 50% Aq. MeOH | -- | -- | -- |
| 5 | 70% Aq. MeOH | -- | -- | -- |
| 6 | 90% Aq. MeOH | -- | ++ | -- |
| 7 | MeOH | -- | ++ | -- |
| 8 | $CH_2Cl_2$ | -- | ++ | -- |
| 1 | $H_2O$ | -- | -- | -- |
| 2 | 10% Aq. MeOH | -- | -- | -- |
| 3 | 30% Aq. MeOH | -- | -- | -- |
| 4 | 50% Aq. MeOH | -- | -- | -- |
| 5 | 70% Aq. MeOH | -- | -- | -- |
| 6 | 90% Aq. MeOH | -- | -- | + |
| 7 | MeOH | -- | -- | * |
| 8 | $CH_2Cl_2$ | -- | -- | -- |

[1]METHICILLIN RESISTANT *STAPHYLOCOCCUS AUREUS* + Activity
++ Strong Activity
[2]VANCOMYCIN RESISTANT ENTEROCOCCUS
*Negligible Activity previously prepared cultures of methicillin resistant *Staphylococcus aureus*, vancomycin resistant enterococcus and *Vibrio vulnificus*, respectively. The results indicate the efficacy of five fractions against each of the indicated pathogens. It is interesting to note that although fraction 2.1 did not show activity against *Vibrio vulnificus* 32 after 12 hours, shows fraction 2.1 is strongly effective against *Vibrio vulnificus* 32 when the experiment proceeds up to 24 hours. The results are tabulated for convenience in Table III below.

As indicated in the above table, the active fractions were 2.1, 3.1 and 4.1. Fractions 2.1 and 3.1 were combined since they exhibited very similar UV spectra. Fraction 4.1 was not combined with other fractions since its UV spectra indicated it was different from the other fractions. Further separation of the combined fractions of 2.1 and 3.1 by HPLC reverse-phase silica gel (C8,250×10 mm, 10$\mu$; 40% MeOH: 50% MeOH: 10% MeCN: $H_2O$: MeOH, at a flow rate of 2.0 milliliter per minute and UV detection at 220 nm) provided five additional major fractions 1.2–5.2. Fractions 2.2, 3.2, 4.2 and 5.2 appear to be effective against methicillin resistant *Staphylococcus aureus*, while fractions 4.2 and 5.2 are effective against vancomycin resistant enterococcus and fractions 2.2 and 3.2 are effective against *Vibrio vulnificus* 32. The results of this are tabulated in Table IV below.

EXAMPLE II

The following experiment demonstrates the ability of the Chaetoceros algae to be used both as a nutrient source and as a means to depurate various aquianimals such as oysters and other mollusks and bivalves. A closed recirculating system was provided as a culture medium for oysters. Chaetoceros algae was co-cultured along with the oyster to achieve a cell density of the algae in the range of $10^4$ to $10^6$ cells per liter of culture medium (sea water). Each of the oysters was known to be infected with *Vibrio vulnificus*. The water in the system was circulated for a sufficient time such that the bivalves would be exposed to and ingest the Chaetoceros algae as food. After three days the oysters were checked for the Vibrio pathogen and were found to be completely free of the bacteria. The natural antibacterial activity of the algae served to cleanse the oyster as it was feeding on the algae. No additional source of antibiotics was incorporated into the circulating water medium.

TABLE III

ACTIVE AGAINST

| Fraction No.[3] | Eluent | Staphylococcus aureus[1] | Enterococcus[2] | Vibrio vulnificus |
|---|---|---|---|---|
| 1.1 | 20% aq. MeOH | -- | -- | -- |
| 2.1 | 40% aq. MeOH | ++ | -- | -- |
| 3.1 | 60% aq. MeOH | ++ | -- | -- |
| 4.1 | 80% aq. MeOH | ++ | -- | -- |
| 5.1 | MeOH | -- | -- | -- |
| CONTROL | None | -- | -- | -- |
| 1.1 | 20% aq. MeOH | -- | + | -- |
| 2.1 | 40% aq. MeOH | -- | ++ | -- |
| 3.1 | 60% aq. MeOH | -- | + | -- |
| 4.1 | 80% aq. MeOH | -- | + | -- |
| 5.1 | MeOH | -- | -- | -- |
| CONTROL | None | -- | -- | -- |
| 1.1 | 20% aq. MeOH | -- | -- | -- |
| 2.1 | 40% aq. MeOH | -- | -- | * |
| 3.1 | 60% aq. MeOH | -- | -- | ++ |
| 4.1 | 80% aq. MeOH | -- | -- | ++ |
| 5.1 | MeOH | -- | -- | -- |
| CONTROL | None | -- | -- | -- |
| 2.1[4] | 40% aq. MeOH | -- | -- | + |

[1]Methicillin Resistant *Staphylococcus aureus*
[2]Vancomycin Resistant Enterococcus
[3]Combination Of: Fractions Previous 5, 6, 7 & 8 from Table I
[4]Fraction No. 2.1 after 24 Hrs.
+Activity
++Strong Activity
*Negligible Activity

TABLE IV

ACTIVE AGAINST

| Fraction No.[3] | Eluent | Staphylococcus aureus[1] | Enterococcus[2] | Vibrio vulnificus |
|---|---|---|---|---|
| 1.2 | 30% aq. MeOH | -- | -- | -- |
| 2.2 | 40% aq. MeOH | ++ | -- | -- |
| 3.2 | 60% aq. MeOH | ++ | -- | -- |
| 4.2 | 80% aq. MeOH | ++ | -- | -- |
| 5.2 | None | ++ | -- | -- |
| CONTROL | | -- | -- | -- |
| 1.2 | 20% aq. MeOH | -- | -- | -- |
| 2.2 | 40% aq. MeOH | -- | -- | -- |
| 3.2 | 60% aq. MeOH | -- | ** | -- |
| 4.2 | 80% aq. MeOH | -- | ++ | -- |
| 5.2 | MeOH | -- | ++ | -- |
| CONTROL | None | -- | -- | -- |
| 1.2 | 20% aq. MeOH | -- | -- | + |
| 2.2 | 40% aq. MeOH | -- | -- | ++ |
| 3.2 | 60% aq. MeOH | -- | -- | + |
| 4.2 | 80% aq. MeOH | -- | -- | * |
| 8.2 | MeOH | -- | -- | -- |
| CONTROL | None | -- | -- | -- |

(1) METHICILLIN RESISTANT *STAPHYLOCOCCUS AUREUS*
(2) VANCOMYCIN RESISTANT ENTEROCOCCUS
+ Activity
++ Strong Activity
*Negligible Activity

EXAMPLE III

Example II was repeated using shrimp as the aquianimal to be cultured. It is known that pathogenic Vibrio bacteria have been associated with the occurrence of shrimp diseases and that this bacteria is often a carrier of virus as well. The shrimp to be cultured were carriers of the bacteria and were placed in the culturing water having a desirable level of Chaetoceros algae present. The cell density of the algae was approximately $10^4$ to $10^5$ cells per liter of sea water. The culture water was circulated in a closed system for sufficient time to allow ingestion of the algae by the shrimp as a nutrient and subsequent depuration of the Vibrio bacteria. After seven days in the culture medium, the shrimp were tested for the presence of Vibrio bacteria. The results indicated that the shrimp had been cleansed of the bacteria.

EXAMPLE IV

Example I was repeated, this time substituting *Vibrio cholerae* as the pathogenic bacteria. The results were identical to Example I.

EXAMPLE V

Examples II–V were repeated using water that contained Chaetoceros at densities varying from $10^4$ to $10^6$ cells per milliliter, but with algae removed. No reduction in the presence of Vibrio bacteria was detected.

EXAMPLE VI 1.2 Kg (wet weight) of algae paste derived from the sample method of Example 1 was homogenized, in MeOH, filtered and concentrated into a crude extract. This crude extract was then loaded onto an Amberlite XAD-2 column (Sigma, 30×7 cm) and step-eluted with the following reagents: Fraction (1) Hexanes, Fraction (2) Toluene, Fraction (3) $CH_2Cl_2$, Fraction (4) EtOAc (ethylacetate). Fractions 1 and 2 contained most of the antibacterial activity and were pooled. The pooled material was then loaded onto a silica gel flash column and eluted with 5:1 to 2:1 Hexanes::ethyl acetate. The eluent was collected into four fractions. Fractions two and three contained most of the reactive material and were pooled. The pooled fractions were then loaded onto a column and eluted in five fractions with ultracarb 5 ODS; 90:10 $MeCN:H_2O$. Fraction 3 was then loaded onto a Silica HPLC column and eluted with 99:1 Hexanes:2-propanol. The major peak was collected and yielded purified Compound II referred to earlier in this application. Fraction 4 was loaded onto a reversed-phase HPLC column and eluted with either Econosil C8, 65% aqueous MeCN or Ultracarb 5 ODS 30, 80% aqueous MeCN. The major peak was collected and yielded purified compound III referred to earlier in this application.

I claim:

1. A composition comprising an antibacterially active extract obtained from the marine algae Chaetoceros, said extract being active against at least one of methicillin resistant *Staphylococcus aureus*, vancomycin resistant enterococcus, *Vibrio vulnificus, Vibrio cholerae, Pseudomona aeruginosa, Listeria monocytogene, Pyrogenes vulgaria, Carynobaster xerosis, Shigella dysenteria, Streptococcus mitis, Streptococcus faecelis, Bacillus subtilis, Bacillus cereus, Micrococcus smegmatis, Micro luteus, Streptococcus puogenes, Proteus vulgaris,* and *Salmonella typhemurium.*

2. A compound having antibacterial properties derived from Chaetoceros algae, said compounding having the formula $$CH_3(CH_2)_n—CH=CH_2CH=CH—(CH_2)_m—R—COOR' \quad (I)$$

wherein n is an integer from 2–8 and m is an integer from 1–8; when present R is $—CH=CH—(CH_2)_p$; and p is an integer from 1–10; R' is H or alkyl $C_{1-10}$ and wherein said compound is active against at least one of methicillin resistant *Staphylococcus aureus*, vancomycin resistant enterococcus, *Vibrio vulnificus, Vibrio cholerae, Pseudomonas aeruginosa, Listeria monocytogene, Pyrogenes vulgaria, Carynobaster xerosis, Shigella dysenteria, Streptococcus mitis, Streptococcus faecelis, Bacillus subtilis, Bacillus cereus, Micrococcus smegmatis, Micro luteus, Streptococcus puogenes, Proteus vulgaris*, and *Salmonella typhemurium*.

3. The composition of claim 1 including one or more biologically active isolates of said extract having the formula

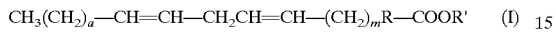 (I)

wherein n is an integer from 2–8 and m is an integer from 1–8; when present R is —CH=CH—$(CH_2)_p$ and p is an integer from 1–10; and R' is H or alkyl $C_{1-10}$; and their pharmaceutically acceptable salts and derivatives thereof.

4. An isolate from the composition of claim 3 having the formula

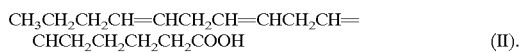 (II).

5. An isolate from the composition of claim 3 having the formula

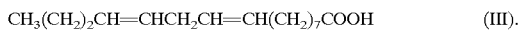 (III).

6. A pharmaceutical composition comprising an antibacterially effective amount of the extract of claim 1 together with a pharmaceutically acceptable carrier.

7. A pharmaceutical composition comprising an antibacterially effective amount of the one or more isolates of claim 3 together with a pharmaceutically acceptable carrier.

8. A method of treating bacterial infections in mammals comprising administering a pharmaceutical composition comprising one or more antibacterially active isolates obtained from the extracts of the marine algae Chaetoceros, said isolates being active against at least one of methicillin resistant *Staphylococcus aureus*, vancomycin resistant enterococcus, *Vibrio vulnificus, Vibrio cholerae, Pseudomonas aeruginosa, Listeria monocytogene, Pyrogenes vulgaria, Carynobaster xerosis, Shigella dysenteria, Streptococcus mitis, Streptococcus faecelis, Bacillus subtilis, Bacillus cereus, Micrococcus smegmatis, Micro luteus, Streptococcus puogenes, Proteus vulgaris*, and *Salmonella typhemurium*.

* * * * *